United States Patent
Su et al.

(10) Patent No.: US 9,782,177 B2
(45) Date of Patent: Oct. 10, 2017

(54) CURVED-HEAD HEMORRHOID BANDING DEVICE

(71) Applicants: Weijia Su, Tyler, TX (US); Qinghua Yang, Irving, TX (US); Xiaotuan Zhao, Harker Heights, TX (US)

(72) Inventors: Weijia Su, Tyler, TX (US); Qinghua Yang, Irving, TX (US); Xiaotuan Zhao, Harker Heights, TX (US)

( * ) Notice: Subject to any disclaimer, the term of this patent is extended or adjusted under 35 U.S.C. 154(b) by 174 days.

(21) Appl. No.: 14/668,456

(22) Filed: Mar. 25, 2015

(65) Prior Publication Data

US 2016/0008000 A1   Jan. 14, 2016

Related U.S. Application Data

(60) Provisional application No. 62/021,994, filed on Jul. 8, 2014.

(30) Foreign Application Priority Data

Nov. 17, 2014  (CN) .......................... 2014 1 0655335
Nov. 17, 2014  (CN) .......................... 2014 2 0689260

(51) Int. Cl.
  *A61B 17/10*  (2006.01)
  *A61B 17/12*  (2006.01)
  *A61B 17/00*  (2006.01)

(52) U.S. Cl.
  CPC .................. *A61B 17/12013* (2013.01); *A61B 2017/00818* (2013.01); *A61B 2017/12018* (2013.01)

(58) Field of Classification Search
  CPC ... A61B 17/12; A61B 17/12013; A61B 17/10; A61B 2017/12018; A61B 2017/00818
  See application file for complete search history.

(56) References Cited

U.S. PATENT DOCUMENTS

2005/0283191 A1* 12/2005 Fontayne ............. A61B 17/072
                                                                606/219

* cited by examiner

*Primary Examiner* — Victor Nguyen
(74) *Attorney, Agent, or Firm* — Kirby B. Drake; Klemchuk LLP

(57) ABSTRACT

A curved-head hemorrhoid banding device may include an inner cylinder curved at one end for sucking the hemorrhoid tissue into the device for banding. The device also may include a curved outer cylinder for releasing a rubber band, a straight barrel for pushing the curved outer cylinder to release the rubber band, an airtight plunger (or operator handle), and a handle for generating negative pressure. The banding device may provide tighter contact with hemorrhoid tissues and thus may provide better suction of hemorrhoid feeding vessels and adjacent rectal mucosal tissue. When being manipulated into contact with the internal hemorrhoid feeding vessel position, the device may maximally fit the anatomic configuration of the rectum, causing less discomfort to the patient during banding and after the procedure. The banding device may be disposable and designed for single-handed use.

5 Claims, 4 Drawing Sheets

CURVED-HEAD HEMORRHOID BANDING DEVICE

CROSS REFERENCE TO RELATED APPLICATIONS

This application claims priority to U.S. Patent Application Ser. No. 62/021,994 filed on Jul. 8, 2014, entitled "Curved-Head Hemorrhoid Banding Device," which is incorporated by reference in its entirety. This application also claims priority to Chinese Patent Application No. 201410655335.7 having a priority date of Nov. 17, 2014 and Chinese Patent Application No. 201420689260.X having a priority date of Nov. 17, 2014, which are incorporated by reference in their entirety.

FIELD OF THE DISCLOSURE

The present disclosure generally relates to hemorrhoid treatment, and more particularly to a curved-head hemorrhoid banding device.

BACKGROUND

Ordinarily, internal hemorrhoids are anatomically located above the anal dentate line on the lateral side of the rectal wall (FIG. 4). Currently, banding is the most commonly used method to treat internal hemorrhoids in a clinical setting. Banding devices available on the market have a straight open head. While such banding devices have been used successfully in hemorrhoid bandings, they have some shortcomings for blind insertion and banding. For example, the operator must be able to grasp the target tissue accurately. Because the banding head may not make good contact with the hemorrhoid tissue, the dentate line of the anus might move upward during the procedure, and the rectal wall muscle layer might be banded instead. This can lead to excessive tissue damage, as well as post-banding complications, especially pain and infection. Further, the operator may need to use an anal scope to locate the hemorrhoid and then insert the head of a straight-head banding device into the rectum to do the banding. However, due to the anatomy of hemorrhoids and the rectum (FIG. 4), the operator often can have difficulty sucking the hemorrhoid tissues into the device (FIG. 5). The main reason is that the hemorrhoid-containing mucosal layer wall of the rectum is parallel to the wall of the banding device, and the opening of the banding device will be almost perpendicular to the tissues to be banded. To maneuver the device head into close contact with the hemorrhoid tissue, the operator may need to repeatedly adjust the device angle or even reinsert it. This can cause pain and discomfort to patients and also can lengthen the procedure time. Besides, the operator can only have very limited room to adjust the angle of the device due to the anatomy of the rectum.

More recently, efforts have been made to overcome the above disadvantages associated with straight-head banding devices. However, shortcomings still exist. For example, with a straight-head device that uses the pressure from a tightly sealed fluid compartment to release the banding rubber or a kinked-head device that uses sealed fluid to push the inner cylinder and then a spring connected to the cylinder to push the outer cylinder to release the banding rubber, these banding devices can be quite complicated and unreliable. In another device, an elastic-type banding tube may be used; however, because the colon wall contracts, it is difficult to bend the tip of the device after it has been inserted into the rectum. Hence this type of device does little to solve the problem that the opening of a banding device may not grasp the targeted hemorrhoid tissue accurately.

SUMMARY

A banding device according to embodiments of the present disclosure may provide tighter contact with hemorrhoid tissues and thus may provide better suction of hemorrhoid tissues and adjacent blood-feeding vessels. When being manipulated into contact with the internal hemorrhoid tissues, the device according to embodiments of the present disclosure may better fit the anatomic configuration of the rectum. Therefore, it targets the desired hemorrhoid tissue more efficiently, causing less discomfort to the patient during banding as well as after the procedure. The banding device is disposable and designed for single-handed use.

Embodiments of the present disclosure may provide a curved-head hemorrhoid banding device comprising an inner cylinder having a curved end that receives a rubber band, a curved outer cylinder, an operator handle, a straight barrel that may receive pressure from the operator handle and pushes the curved outer cylinder forward to rotate along the inner cylinder and release the rubber band from the curved end of the inner cylinder, and a handle that generates negative pressure on the device causing hemorrhoid tissues to be sucked into the device. The operator handle may be an airtight plunger. The banding device also may include a knob on the inner cylinder to ensure that the curved outer cylinder rotates along an open track. The straight barrel may push the curved outer cylinder through two half circles causing the curved outer cylinder to rotate smoothly along the inner cylinder. The banding device also may include a plunger knob, a barrel track, and a barrel flange, wherein the plunger knob and the barrel track operate so that the barrel flange may control the direction of the curved head of the banding device. The rubber band may be formed of silicon. The banding device may be formed of plastic. The curved end of the inner cylinder may have an arc length of approximately 60 degrees and the curved outer cylinder may have an arc length of approximately 45 degrees. The centers of the arcs of the inner cylinder and the curved outer cylinder may be at approximately the same location within the banding device. The curved outer cylinder may also include a track end that is sealed with a small cross-shaped part after the curved outer cylinder is placed over the inner cylinder. The inner cylinder and the operator handle may be solidly affixed to one another. The banding device may be disposable. The banding device may be designed for single-handed use.

Other embodiments of the present disclosure may provide a curved-head hemorrhoid banding device comprising an inner cylinder having a curved end that may receive a rubber band, a curved outer cylinder having a track portion with an open end and a closed end, wherein the curved outer cylinder may be placed over the inner cylinder, and a straight barrel that may push the curved outer cylinder forward to rotate along the track portion between the open end and the closed end and release the rubber band from the curved end of the inner cylinder. The banding device may further comprise an operator handle that may be pulled to cause negative pressure for hemorrhoid tissues to be sucked into the device. The operator handle may further comprise a plunger knob positioned at the end of the operator handle adjacent to the straight barrel to prevent the straight barrel from rotating when the straight barrel pushes the curved outer cylinder forward. The arc length of the curved end of the inner cylinder and the arc length of the curved outer cylinder may differ by approximately 15 degrees. The curved end of the inner cylinder may have an arc length of approximately 60 degrees and the curved outer cylinder may have an arc length of approximately 45 degrees.

Additional embodiments of the present disclosure may provide a method of using a curved-head hemorrhoid banding device comprising placing a rubber band on an end of a curved inner cylinder, inserting the end of the curved inner cylinder into the rectum, and pushing a barrel flange that may cause a straight barrel attached to the curved inner cylinder to push a curved outer cylinder of the device forward to rotate along the curved inner cylinder and release the rubber band from the end of the curved inner cylinder. The method may further comprise pulling a handle to cause negative pressure for hemorrhoid tissues to be sucked into the device.

Other technical features may be readily apparent to one skilled in the art from the following figures, descriptions and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

Figure 1:
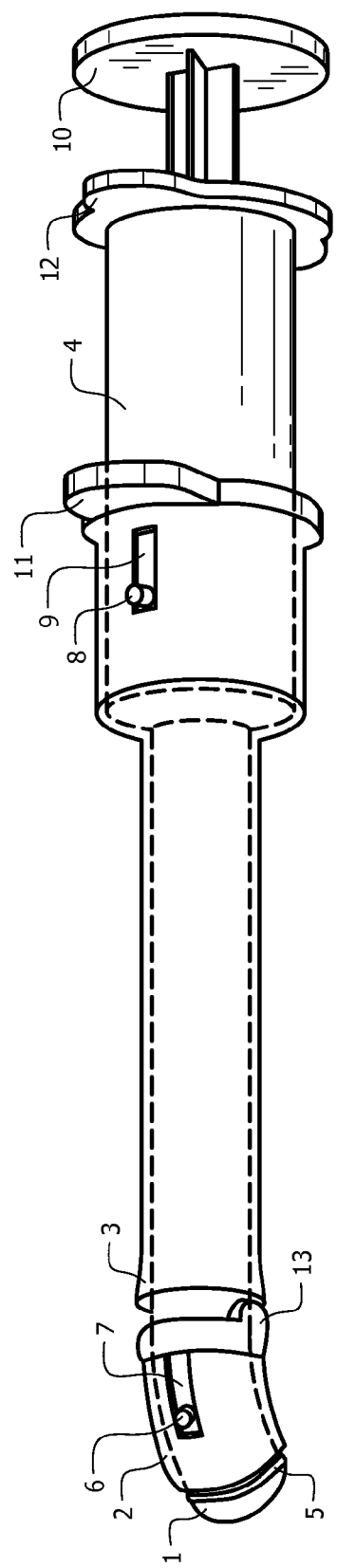
FIG. 1 depicts an overall view of a curved-head hemorrhoid banding device according to an embodiment of the present disclosure.

A curved-head hemorrhoid banding device according to embodiments of the present disclosure (as depicted, for example, in FIGS. 1, 2 and 3) may include inner cylinder 1 that may be curved at one end for sucking the hemorrhoid tissue into the device for banding, curved outer cylinder 2 for releasing rubber band 5, straight barrel 3 for pushing curved outer cylinder 2, air-tight plunger 4 (which also may be referred to as the operator handle), and handle 10 for generating negative pressure. Straight barrel 3 may push curved outer cylinder 2 through two half circles 13, causing it to rotate smoothly along inner cylinder 1 and release rubber band 5 more easily and smoothly. Inner cylinder 1 may include knob 6 to ensure that curved outer cylinder 2 may effectively rotate along open track 7. Plunger knob 8 and barrel track 9 may guarantee that barrel flange 11 may control the direction of the curved head of the device according to embodiments of the present disclosure.

While inner cylinder 1 and curved outer cylinder 2 have been described as cylinders, it should be appreciated that they may assume other rounded or tubular shapes without departing from the present disclosure. In embodiments of the present disclosure, rubber band 5 may be latex-free or may be regular rubber. In an embodiment of the present disclosure, rubber band 5 may be formed of silicon. However, rubber band 5 may be formed of other similar materials without departing from the present disclosure. In embodiments of the present disclosure, the banding device may be formed out of plastic or another similar material. It should be appreciated that the material forming the device may be opaque or clear without departing from the present disclosure.

Compared with traditional straight-head hemorrhoid banding devices, a curved-head hemorrhoid banding device according to embodiments of the present disclosure may provide tighter contact with hemorrhoid tissues and thus may provide better suction of hemorrhoid tissues and adjacent blood-feeding vessels. The device according to embodiments of the present disclosure may be handled with just one hand—a feature that may decrease the procedure time. The device according to embodiments of the present disclosure may provide more accurate hemorrhoid banding, thereby decreasing a patient's pain and discomfort. This is because when a device according to embodiments of the present disclosure is being manipulated into contact with internal hemorrhoid tissues, it may better fit the anatomical configuration of the rectum, causing less discomfort to the patient both during banding as well as after the procedure. It may also result in fewer post-procedure complications.

Figure 2:
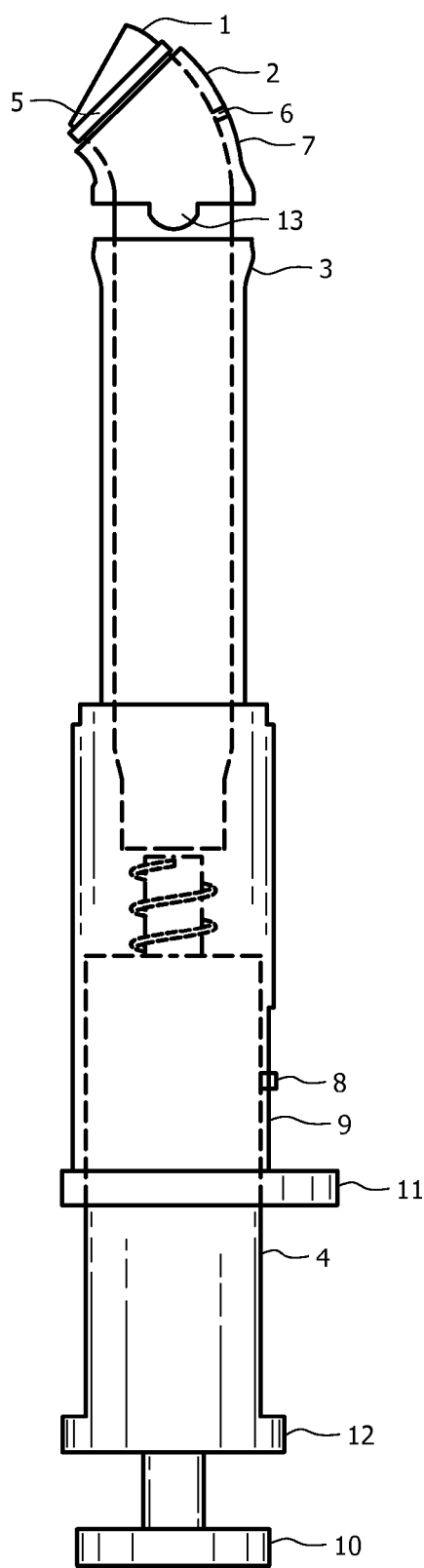
FIG. 2 depicts a side view of a banding device according to an embodiment of the present disclosure, the device comprising a curved inner cylinder, a curved outer cylinder, a straight barrel, and a plunger.
Figure 6:
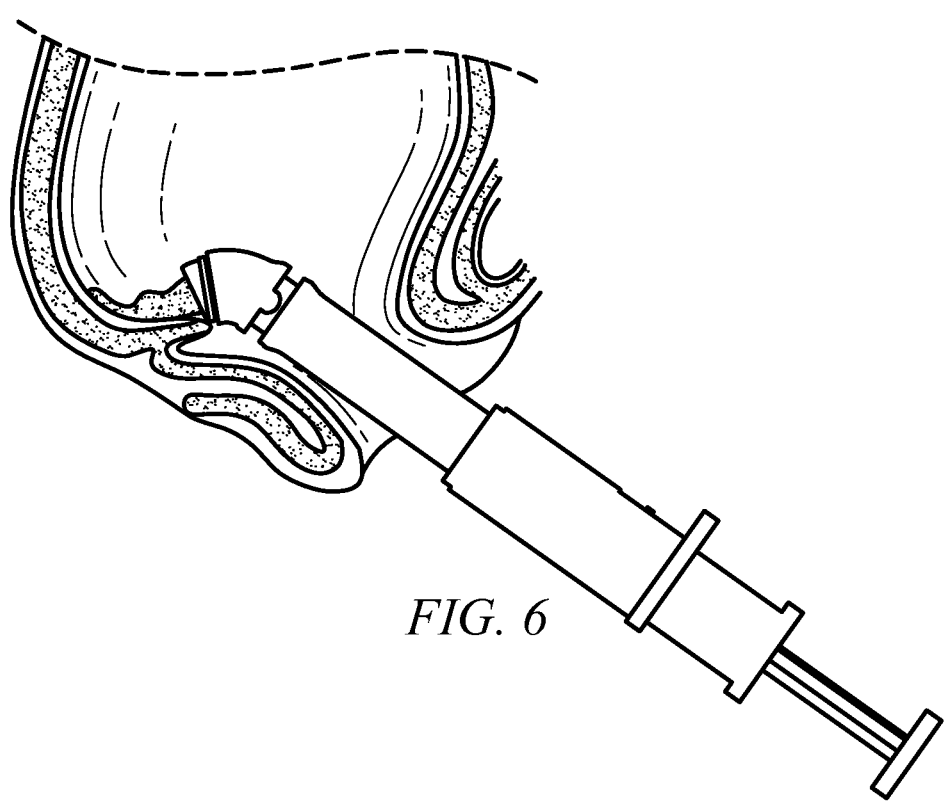
FIG. 6 depicts operation of a curved-head banding device according to an embodiment of the present disclosure.

To overcome the shortcomings of currently available straight-head hemorrhoid banding devices, a hemorrhoid banding device according to embodiments of the present disclosure may include a curved head as depicted in FIG. 2. By having a curved end on inner cylinder 1 as well as curved outer cylinder 2, the device according to embodiments of the present disclosure may provide better contact with hemorrhoid tissue and the feeding vessel at the lateral wall of rectum. It should be appreciated that a device according to embodiments of the present disclosure may be used with an anal scope or may be used alone in the case of blind insertion. The device may minimally grasp the deeper layer tissue bellow the mucosa in the rectum (such as depicted in FIG. 6) and may greatly reduce tissue damage and post-banding complications. The curved-head banding device according to embodiments of the present disclosure may be designed for the anatomic configuration at the junction of the rectum and anus, where the three main hemorrhoid feeding vessels start to branch small vessels into many individual internal hemorrhoids. The design of the device according to embodiments of the present disclosure may greatly increase the area of contact with the hemorrhoid tissue, and thus provide better suction of the tissues that contain hemorrhoid feeding vessels to be banded.

FIG. 2 depicts that the curved end of inner cylinder 1 may have an arc length of approximately 60 degrees while curved outer cylinder 2 may have an arc length of approximately 45 degrees. By having an approximately 15-degree difference between the inner and outer cylinder arc lengths, there may be enough space provided to place rubber band 5. Rubber band 5 may be stretchable or stretched and be placed at the tip of inner cylinder 1 prior to beginning the procedure. It should be appreciated that the centers of these arcs should be at approximately the same location to ensure a smooth rotation of curved outer cylinder 2. Including knob 6 on inner cylinder 1 and open track 7 on curved outer cylinder 2 may better ensure that curved outer cylinder 2 may rotate relative to the center of the arc as opposed to the cylinder cross-sectional center.

Figure 3:
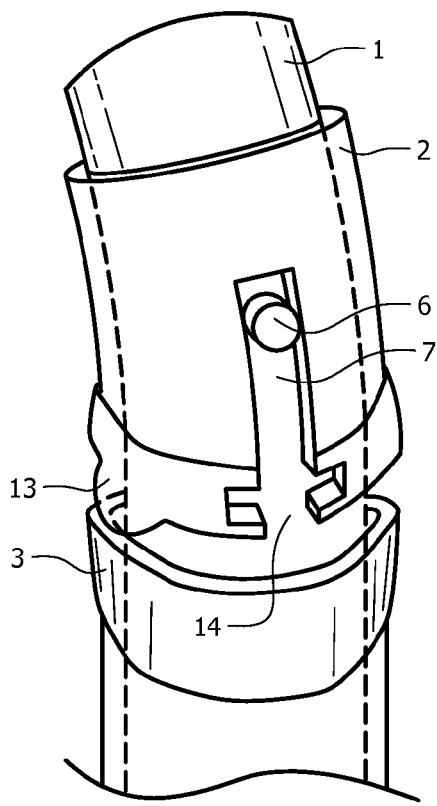
FIG. 3 depicts a curved head according to an embodiment of the present disclosure.

FIG. 3 depicts additional details of curved outer cylinder 2 in relation to inner cylinder 1 having a curved end according to embodiments of the present disclosure. It should be appreciated that the track end on curved outer cylinder 2 may be sealed with a small cross-shaped part of the same size as cross opening 14 after curved outer cylinder 2 may be placed over inner cylinder 1. FIG. 3 depicts that open track 7 does not reach the end of curved outer cylinder 2. This design feature may assist in guaranteeing that curved outer cylinder 2 will not dislodge into the rectum during a procedure. Inclusion of plunger knob 8 at the lower end of plunger 4 may guarantee that straight barrel 3 will not rotate. This feature may ensure that the thumb push will provide the operator with ability to better direct the curved head of the device even after the curved head has been inserted into the rectum.

It should be appreciated that inner cylinder 1 and plunger 4 may be glued together or otherwise solidly affixed to one another according to embodiments of the present disclosure. Accordingly, this connection between inner cylinder 1 and plunger 4 may be airtight.

Inner cylinder 1 may have an outer diameter of approximately 11.5 mm. The inner diameter of cylinder 1 may be approximately 9.7 mm. Cylinder 1 may be curved on one end, with a radius of curvature of approximately 20 mm. Knob 6 that may guide movement of curved outer cylinder 2 may be located about 30 degrees from the starting point of the curvature. The total length of inner curved cylinder 1 may be approximately 90 mm. While certain dimensions have been provided herein, it should be appreciated that the dimensions may be larger or smaller to accommodate the needs of the patient or the operator without departing from the present disclosure.

Curved outer cylinder 2 may have an outer diameter of approximately 13.8 mm and an inside diameter of approximately 12 mm. Like inner curved cylinder 1, the radius of curvature for curved outer cylinder 2 may also be approximately 20 mm. This may better ensure that curved outer cylinder 2 can rotate smoothly along the curved end of inner cylinder 1. Again, while certain dimensions have been provided herein, it should be appreciated that the dimensions may be larger or smaller to accommodate the needs of the patient or the operator without departing from the present disclosure.

Straight barrel 3 may have an outer diameter of approximately 13.8 mm at a first end and an outer diameter of approximately 28 mm at a second end. Again, while certain dimensions have been provided herein, it should be appreciated that the dimensions may be larger or smaller to accommodate the needs of the patient or the operator without departing from the present disclosure. Barrel track 9 that may guide the direction of the curved head of the device may be located at one end (as depicted, for example, in FIG. 2). After straight barrel 3 has been assembled, it should be appreciated that plunger 4 may be glued or otherwise solidly affixed to inner cylinder 1. Excluding the handle, plunger 4 may be approximately 75 mm in length. Barrel flange 11 may be used to guide the direction of inner cylinder 1 and push curved outer cylinder 2. Flange 12 may be located at one end of plunger 4 according to embodiments of the present disclosure. It may help with one-handed operation of pulling of handle 10 to cause negative pressure.

A device according to embodiments of the present disclosure may be used as follows. Rubber band 5 may be placed on the tip/end of curved inner cylinder 1. The tip/end of the device may be inserted into the rectum, making sure that it is being aimed at the hemorrhoid tissues to be banded. It should be appreciated that the hemorrhoid tissues may be located by using an anal scope or by finger rectal examination according to embodiments of the present disclosure. Handle 10 may be pulled to cause negative pressure so that the hemorrhoid tissues may be sucked into the device. During this portion of the process, care should be taken to ensure that the patient is not experiencing pain or discomfort. An operator may then use his/her thumb to push barrel flange 11. This force may cause straight barrel 3 to move forward and for curved outer cylinder 2 to rotate and eventually release rubber band 5. Finally, the device may be pulled out as the hemorrhoid banding is completed. While certain steps have been described herein, it may be appreciated that more or fewer steps may be performed without departing from the present disclosure.

Figure 4:
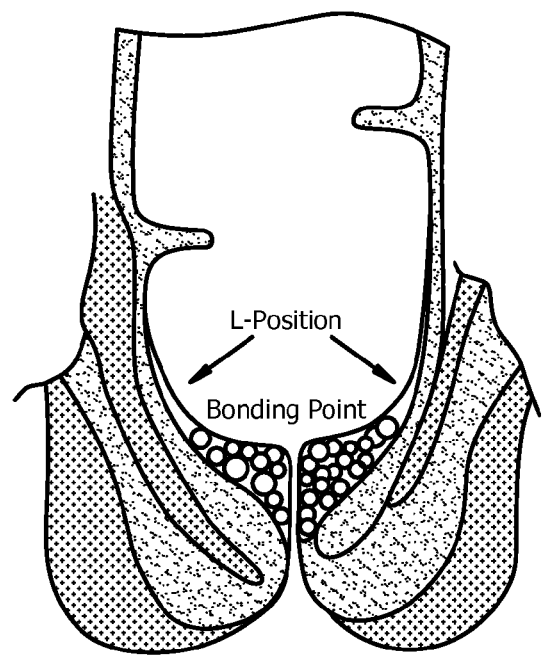
FIG. 4 depicts a diagram of internal hemorrhoids.
Figure 5:
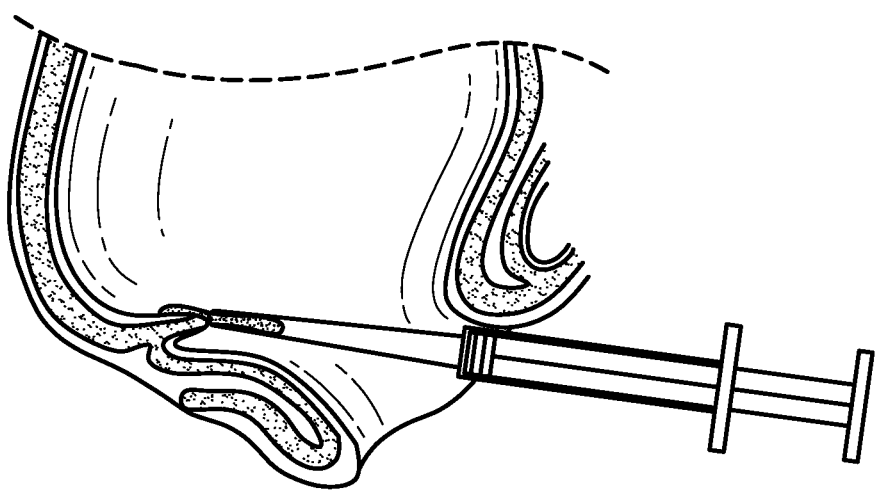
FIG. 5 illustrates the banding process of a straight-head banding device according to the prior art.

The curved-head hemorrhoid banding device according to embodiments of the present disclosure may provide several advantages over devices and methods that have been previously used. Anatomically, internal hemorrhoid feeding vessels are usually located above the dentate line and are covered by rectal mucosa (as depicted in FIG. 4). The internal hemorrhoids are congested and dilated blood vessels and usually distribute as cluster form under the rectal mucosa. Studies show that stopping the three main feeding vessels of a hemorrhoid clusters is more effective than treating the individual hemorrhoids one by one. Accordingly, the banding site should be located above the dentate line, where there are almost no pain nerves.

When a straight-head banding device has been used to band a hemorrhoid, after such a device has been inserted into the rectum, the device opening may be nearly perpendicular to the hemorrhoid tissue. Accordingly, the operator has to pull the device back, making multiple adjustments of the insertion angle to locate the opening of the device to the best banding point before releasing the rubber band. These maneuvers often cause discomfort, pain, or mucosal injuries (laceration) for the patient. The operator also needs to tilt the banding device, which causes the anal dentate line to move upward. As a consequence, tissue below the dentate line may also be banded, which can produce post-banding complications. With a straight-head banding device, an operator is less able to control the pressure on the mucosal surface of the hemorrhoids, since the device opening is at a suboptimal angle for surface contact with the mucosa. As a result, the rubber band is sometimes place too close to the dentate line, causing post-banding pain and discomfort.

As described, a traditional straight-head hemorrhoid banding device may have poor contact with hemorrhoid tissue owing to its straight head. The operator needs to tilt the device in order to gain tighter contact with hemorrhoid tissues. Additionally, flexible banding devices, when inserted into the rectum, may be difficult to bend, owing to pressure from colon tissue. In contrast, a curved-head hemorrhoid banding device according to embodiments of the present disclosure can be inserted into the rectum in a desired direction. It may decrease patient pain and discomfort. It also may provide a better suction for sucking the hemorrhoid tissue and surrounding blood-feeding vessels. It can be handled with just one hand, and thus may require less time for a procedure. Moreover, a device according to embodiments of the present disclosure may fit the anatomic configuration of the rectum more comfortably. More comfortable banding may decrease a patient's pain and discomfort, and may reduce complications after banding. A device according to embodiments of the present disclosure also may make it considerably easier to perform the hemorrhoid banding procedure. The curved head of a device according to embodiments of the present disclosure may gently push open the contracted anus sphincter and may reduce discomfort in comparison with the traditional straight-head banding devices, which may be difficult to blindly insert into the anal canal without causing discomfort.

Anatomically, the shape of curved head of a device according to embodiments of the present disclosure may better fit the L-shaped rectal anus transition zone above the dentate line, where blood-feeding vessels for hemorrhoids are located. A device according to embodiments of the present disclosure may achieve greater contact with hemorrhoid tissues, and thus may more efficiently apply evenly distributed suction to grasp the hemorrhoid feeding vessel within the mucosa layer. With a curved-head banding device according to embodiments of the present disclosure, an operator does not need to tilt the device in order to position the opening on the right point at L-shaped rectal anus transition zone for the hemorrhoid banding procedure. A curved-head banding device according to embodiments of the present disclosure will minimize the up-movement of the dentate line, and thus may avoid placing the band too close to the dentate line.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

The invention claimed is:

1. A curved-head hemorrhoid banding device comprising:
   a rubber band; an inner cylinder having a curved end that receives the rubber band;
   a curved outer cylinder having a track portion with an open end and a closed end, wherein the curved outer cylinder is placed over the inner cylinder; and
   a straight barrel that pushes the curved outer cylinder forward to rotate along the track portion between the open end and the closed end and releases the rubber band from the curved end of the inner cylinder.

2. The banding device of claim 1 further comprising:
   an operator handle that is pulled to cause negative pressure for hemorrhoid tissues to be sucked into the device.

3. The banding device of claim 2, the operator handle further comprising:
   a plunger knob positioned at the end of the operator handle adjacent to the straight barrel to prevent the straight barrel from rotating when the straight barrel pushes the curved outer cylinder forward.

4. The banding device of claim 1 wherein an arc length of the curved end of the inner cylinder and an arc length of the curved outer cylinder differ by approximately 15 degrees.

5. The banding device of claim 4 wherein the arc length of the curved end of the inner cylinder is approximately 60 degrees and the arc length of the curved outer cylinder is approximately 45 degrees.

* * * * *